United States Patent [19]

Kerwar et al.

[11] Patent Number: 4,617,319
[45] Date of Patent: Oct. 14, 1986

[54] METHOD OF TREATING MULTIPLE SCLEROSIS

[75] Inventors: Suresh S. Kerwar, Ossining; Adolph E. Sloboda, New City; Susan C. Ridge, Valley Cottage, all of N.Y.

[73] Assignee: American Cyanamid Company, Stamford, Conn.

[21] Appl. No.: 744,370

[22] Filed: Jun. 13, 1985

[51] Int. Cl.$^4$ .......................................... A61U 31/135
[52] U.S. Cl. .................................................... 514/647
[58] Field of Search ........................................ 514/647

Primary Examiner—Stanley J. Friedman
Attorney, Agent, or Firm—Susan H. Rauch

[57] ABSTRACT

A method of treating neuroimmunologic diseases such as multiple sclerosis and acute disseminated encephalomyelitis using 1,4-dihydroxy-5,8-bis[[(2-hydroxyethylamino)ethyl]amino]anthraquinone, or a pharmacologically acceptable acid addition salt thereof.

8 Claims, No Drawings

METHOD OF TREATING MULTIPLE SCLEROSIS

SUMMARY OF THE INVENTION

This invention is concerned with a method of treating neuroimmunologic diseases such as multiple sclerosis and acute disseminated encephalomyelitis using the cytotoxic drug referred to by the registered trademark "NOVANTRONE".

"NOVANTRONE" brand 1,4-dihydroxy-5,8-bis[[(2-hydroxyethylamino)ethyl]amino]anthraquinone, dihydrochloride has the following structure:

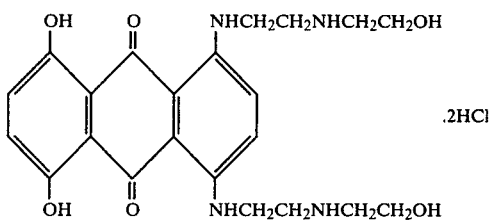

and is described and claimed in U.S. Pat. No. 4,197,249.

"NOVANTRONE" has shown antineoplastic activity against a variety of experimental tumors as described in the following references:

Murdock, K. C., et. al., J. Med. Chem., 22, 1024(1979).
Wallace, R. E., et. al., Cancer Res., 39, 1570(1979).
Murray, E. F. and Wallace, R. E., Anthracyclines: Current Status and New Developments. Acad. Press, N.Y., 397(1980).
Wallace, R. E., et. al., Am. Acad. Can. Res., 49A(1981).
Wallace, R. E., et. al., Am. Acad. Can. Res., 767A(1982).
Durr, F. E., et. al., Cancer Treatment Reviews. Supplement B., Acad. Press, N.Y.(1983).

Clinical studies with "NOVANTRONE" have indicated that it is active against a variety of human tumors as described in the following references:

Colton, C. A., Invest. New Drugs, 1, 65(1983).
Knight, W. A., et. al., Invest. New Drugs, 1, 181(1983).
Smith, I. E., Cancer Treat. Revs., 10, 103(1983).

Mechanistic studies with "NOVANTRONE" have shown that it intercalates with DNA, is a potent inhibitor of both DNA and RNA synthesis, induces scissions in single and double stranded DNA and can block the cell cycle in the G2 phase.

Preclinical studies with "NOVANTRONE" have shown that, unlike some anthracycline derivatives, it does not induce the formation of free radicals nor does it induce lipid peroxidation, which accounts for its low cardiotoxicity in animals and humans as described in the following references:

Doroshow, J. H., Clin Res., 31, 67A(1981).
Karash, E. D., and Novak, R. F., Biochem. Biophys. Res. Comm., 108, 1346(1982).
Mimnaugh, E. G., et. al., Cancer Res., 42,3574(1982).

Experimental Allergic Encephalomyelitis (EAE) is considered by those skilled in the pharmacology of neuroimmunologic diseases to be an animal model of neuroimmunologic diseases such as multiple sclerosis and acute disseminated encephalomyelitis. Agents that suppress animal EAE lesions are considered to be of potential clinical utility in the treatment of neuroimmunologic diseases. For example, a number cytotoxic agents have been shown to suppress experimental allergic encephalomyetlitis (EAE) lesions in animals. Some of these agents have shown clinical efficacy in patients with multiple sclerosis as described in the following references:

Rosenthale, M. E., et. al., Arch. Int. Pharmacodyn, 179,251(1969).
Levine, S. and Wenk, E. J., Am. J. Pathol. 47, 61(1965).
Levine, S. and Sorwinski, R., Arch. Int. Pharmacodyn., 230, 309(1977).
Paterson, P. Y. and Hanson, M. A., J. Immunol., 103, 1311(1969).
Ellison, G. W., and Myers, L. W., Neurology, 28, 132(1978).

The most widely clinically studied of these cytoxic agents is cyclophoshamide. A controlled study has recenty shown a regimen of cyclophasphamide plus ACTH to be capable of stabilizing the clinical course of patients with severe progressive multiple sclerosis and in some cases improving their condition. (Hauser, S. L. et al., N. Engl. J. Med., 308, 173 (1983)).

It has now been discovered that "NOVANTRONE" suppresses both active EAE induced by myelin basic protein and passive EAE induced by sensitized spleen cells.

Treatment of rats having either developing or established experimental allergic encephalomyelitis (EAE) with "NOVANTRONE" suppressed the hind limb paralysis associated with the disease. Histopathological examination of the spinal cords of these rats showed that "NOVANTRONE"—treated rats were devoid of the vascular lesions associated with EAE. Spleen cells derived from immunized rats that had been treated in vivo with "NOVANTRONE" did not transfer disease when these cells were administered to naive syngeneic recipients. In addition, spleen cells from diseased rats did not transfer EAE lesions when these cells were administered to recipients that had been treated with "NOVANTRONE". Recipients treated with "NOVANTRONE" were resistant to EAE lesions induced by sensitized cells in a rapid passive transfer system. When spleen cells from rats with EAE were incubated in vitro with "NOVANTRONE", these cells did not transfer disease to recipients.

DESCRIPTION OF THE INVENTION

The compound "NOVANTRONE" was tested by the procedures described below.

Preparation of Myelin Basic Protein

Myelin basic protein (MBP) was isolated from guinea pig spinal cord (Pel-Freeze, Rogers, Ark.) by a modification of the procedure of Diebler, G. E., et. al., Prep. Biochem., 2, 139(1972). A 40 g portion of frozen guinea pig spinal cord was homogenized in 600 ml of cold chloroform:methanol (400:200 v/v) and extracted overnight. The residue was collected by filtration, washed with cold water and extracted with 80 ml of 0.01N hydrochloric acid (pH 3.0–3.2) in the cold. The acid extract was centrifuged at 48,000 Xg. Sufficient solid ammonium sulfate was added to the supernatant to provide 50% saturation, then the precipitate was collected by centrifugation. The precipitate was dissolved in 0.01N hydrochloric acid and dialyzed exhaustively against cold water. After neutralization and clarification the clear supernatant was lyophilized providing a powder (MBP) which was used to immunize rats.

Induction of Experimental Allergic Encephalomyelitis (EAE)

Male inbred Lewis rats weighing 150–160 g (Charles River Breeding Laboratories, Wilmington, Mass.) were immunized in the hind footpad with 25 μg of MBP that was emulsified in 0.05 ml of incomplete Freund's adjuvant containing 100 μg of *Mycobacterium tuberculosis.* With this schedule, hind limb paralysis in the immunized rats occurred between day 10 and day 12 post immunization.

To compare the effects of "NOVANTRONE" with cyclophosphamide on EAE, these agents were administered intraperitoneally either on the day of immunization (developing lesion) or 7 days after antigen administration (established lesion).

Passive EAE Induced by Cultured Spleen Cells

Between day 12 and day 14 post immunization, spleens were removed and single cell suspensions were prepared essentially by the method of Fidler, J., J. Immunol., 121, 1558(1978). The cells were cultured for 72 hours at 37° C. in a tissue culture incubator at a density of $2 \times 10^6$ cells/ml in RPMI-1640 (GIBCO) medium supplemented with 2 mM glutamine, 100 μg/ml of penicillin, 100 μg/ml of streptomycin, 5% heat inactivated fetal calf serum, $2 \times 10^{-5}$ mercaptoethanol and 2 μg/ml of MBP as described by Holde, J. H., et. al., J. Immunol. 130, 732(1983). After culture, the cells were harvested, washed and the number of viable cells determined by dye exclusion. Between 4 and $6 \times 10^7$ cells were injected intraperitoneally into naive syngeneic recipients.

To determine the in vitro effect of "NOVANTRONE" on adoptive transfer of EAE, spleen cells prepared as above were incubated with 2 μg/ml of MBP and 0.1 or 0.01 μg/ml of "NOVANTRONE". After 72 hours in culture, the cells were harvested and between 4 and $6 \times 10^7$ viable cells were injected intraperitoneally into naive syngeneic recipients. The recipient rats were monitored for clinical signs of EAE every 24 hours.

In some experiments, the recipient rats were pretreated with 0.5 mg/kg/day of "NOVANTRONE" for 5 days before the intraperitoneal transfer of sensitized spleen cells. "NOVANTRONE" treatment of the recipients was stopped upon cell transfer.

In a rapid transfer system, described by Levine, S. and Hoenig, E. H., J. Immunol., 100, 1310,(1968), recipients were subjected to thermal injury 2 days before cell transfer. The Levine and Hoenig study has shown that thermal injury accelerates and localizes EAE lesions. The recipients were treated intravenously with $2 \times 10^8$ sensitized lymph node cells. Recipients were sacrificed at 24 hours and the EAE was evaluated histologically by the method of Levine and Hoenig.

Neurologic Assessment of EAE

Clinical signs of EAE were graded as follows:
0 = Normal
1 = flaccid tail
2 = hind quarter weakness
3 = hind quarter paralysis with incontinence Histological Assessment of EAE At sacrifice, the spinal cords were removed and fixed by the method of Levine and Hoenig. Longitudinal sections of the spinal cord were prepared and stained with hematoxylin-eosin. The stained sections were scored on a scale of zero (no vascular inflammatory lesions) to 4 (all vessels involved). These scores reflect the extent and severity of lesions so that a score of 1 is assigned to a cord showing 1 or few lesions and 4 to a cord in which almost every vessel is involved.

Results and Discussion

The effect of "NOVANTRONE" on the developing and established lesions of EAE was compared with that of cyclophosphamide. As Table I illustrates, intraperitoneal doses of 0.5 and 0.25 mg/kg/day of "NOVANTRONE" significantly suppressed the clinical symptoms and histological lesions associated with developing EAE. At 0.125 mg/kg/day, "NOVANTRONE" treatment delayed the onset of the disease but the severity of the histological lesions was unaffected. By contrast, intraperitoneal administration of cyclophosphamide suppressed the clinical symptoms and histological lesions associated with developing EAE at a dosage level of 5 mg/kg/day. At 2.5 mg/kg/day cyclophosphamide delayed the onset of clinical symptoms but had no effect on the severity of the disease. At 1.25 mg/kg/day cyclophosphamide treatment had no effect.

These results show that "NOVANTRONE" is at least 10 to 20 times more potent than cyclophosphamide in suppressing both the clinical symptoms and histological lesions associated with developing EAE.

Moreover, histopathological examination of the spinal cord sections of 3 EAE rats (control) showed perivascular cuffs with several layers of mononuclear cells. Foci of gliosis were present, especially in the lumbosacral region. Mitotic figures in the astrocytes were rarely encountered. Mononuclear cells were also present in areas distant from the blood vessels. In rats treated with 0.5 mg/kg/day of Novantrone ™ none of the spinal cords of the three rats examined had vascular inflammatory lesions. In rats treated with 5 mg/kg/day of cyclophosphamide a perivascular cuff of mononuclear cells was detected in one of the three rats examined.

TABLE I

Effect of "NOVANTRONE" and Cyclophosphamide on Developing EAE

| Compound and Daily Dose (mg/kg)** | No. of Rats | Paralysis Grade (± SEM) on Day | | | | | Histological Grade (± SEM) on Day 16 |
|---|---|---|---|---|---|---|---|
| | | 12 | 13 | 14 | 15 | 16 | |
| Control | 18 | 1.0 ± 0.2 | 1.7 ± 0.2 | 2.1 ± 0.2 | 1.9 ± 0.2 | 0.6 ± 0.1 | 3.0 ± 1 |
| "NOVANTRONE" | | | | | | | |
| 0.5 | 18 | 0 ± 0* | 0 ± 0* | 0 ± 0* | 0 ± 0* | 0 ± 0* | 0 ± 0* |
| 0.25 | 18 | 0 ± 0* | 0 ± 0* | 0.3 ± 0.1* | 0.3 ± 0.1 | 0.1 ± 0.1* | 0.6 ± 0.4* |
| 0.125 | 18 | 0.2 ± 0* | 0.9 ± 0.1* | 2.2 ± 0.2 | 1.8 ± 0.1 | 0.4 ± 0.1 | 2.6 ± 0.4 |
| Cyclophosphamide | | | | | | | |
| 5 | 18 | 0 ± 0* | 0 ± 0* | 0 ± 0* | 0 ± 0* | 0 ± 0* | 0.3 ± 0.1* |
| 2.5 | 18 | 0 ± 0* | 0 ± 0* | 0 ± 0* | 1.5 ± 0.3 | 2.4 ± 0.3 | 2.6 ± 0.3 |
| 1.25 | 18 | 0 ± 0* | 0.2 ± 0.1* | 0.9 ± 0.2* | 1.5 ± 0.2 | 2.1 ± 0.3 | 3.0 ± 0.3 |

*p ≤ 0.05 as compared to control
**Treatment with agents instituted on day zero

To determine if a daily treatment regimen was required, "NOVANTRONE" was administered to different groups of rats on a daily, alternate day or weekly basis. The results appear in Table II and show that "NOVANTRONE" administered intraperitoneally on alternate days at doses ranging from 1 to 0.25 mg/kg suppressed the clinical lesions associated with developing EAE. "NOVANTRONE" administered at a dose of 3.5 mg/kg once a week was also effective. However, weekly doses of 1.75 or 0.88 mg/kg were ineffective.

TABLE II

Effect of Varying Dosing Schedule of "NOVANTRONE" on Developing EAE

| "NOVANTRONE" Administration | | | |
|---|---|---|---|
| Dose (mg/kg)** | Schedule | No. of Rats | Paralysis Grade (±SEM) Day 14 |
| Control | | 18 | 2.3 ± 0.2 |
| 0.5 | Daily | 9 | 0.11 ± 0.11* |
| 0.25 | Daily | 9 | 0.22 ± 0.14* |
| 1.0 | Alternate days | 9 | 0. ± 0* |
| 0.5 | Alternate days | 9 | 0.44 ± 0.39* |
| 0.25 | Alternate days | 9 | 0.25 ± 0.25* |
| 3.5 | Once per week | 9 | 0.33 ± 0.1* |
| 1.75 | Once per week | 9 | 1.44 ± 0.4 |
| 0.88 | Once per week | 9 | 2.33 ± 0.3 |

*$p \leq 0.05$
**Treatment initiated on day zero

The effect of "NOVANTRONE" and cyclophophamide on established EAE is shown in Table III. As with developing EAE, "NOVANTRONE" at doses of 0.5 and 0.25 mg/kg/day suppressed the clinical symptoms and histological lesions associated with established EAE. Cyclophosphamide at 5 and 2.5 mg/kg/day suppressed clinical symptoms but the severity of the histological lesions was not decreased at the 2.5 mg/kg dose.

TRONE"—treated rats had been cultured in vitro with MBP.

TABLE IV

Spleen Cells From Immunized, "NOVANTRONE"-Treated Animals Are Unable To Transfer EAE To Normal Syngeneic Recipients

| Donors | No. of Rats | Paralysis Grade of Recipients (±SEM) | Incidence of Paralysis in Recipients | Histological Grade (±SEM) |
|---|---|---|---|---|
| EAE Control | 6 | 1 ± 0 | 6/6 | 3.0 ± 0 |
| Novantrone TM Treated (0.5 mg/kg) | 5 | 0 ± 0* | 0/5* | 0 ± 0* |

*$p \leq 0.05$ as compared to recipient rats treated with EAE control cells.

Spleen cells from EAE animals were incubated in vitro for 72 hours with MBP alone and MBP plus "NOVANTRONE". Cells were harvested and injected intraperitoneally into normal recipients. Determinations of Paralysis Grade, Incidence of Paralysis and Spinal Cord Histology Grade were made on day 7 post transfer.

Spleen cells from animals with EAE, when cultured with MBP and "NOVANTRONE" at 0.1 and 0.01 μg/ml, were unable to transfer disease to recipients, as shown in Table V. Histological examination of the spinal cord of recipients showed no lesions. Since viable cells were transferred, the lack of disease induction cannot be attributed to nonspecific toxicity. Therefore, it is believed that "NOVANTRONE" at these concentrations, either prevents the proliferation of MBP-sensitized T cells or inhibits the conversion of MBP-sensitized T cells into T effector cells during culture. Because cellular proliferation in vitro is not required for the

TABLE III

Effect of "NOVANTRONE" and Cyclophosphamide on Established EAE

| Compound and Daily Dose (mg/kg)** | No. of Rats | Paralysis Grade (± SEM) on Day | | | | | Histological Grade (± SEM) on Day 16 |
|---|---|---|---|---|---|---|---|
| | | 12 | 13 | 14 | 15 | 16 | |
| Control | 18 | 1.2 ± 0.2 | 2.2 ± 0.2 | 2.2 ± 0.2 | 1.8 ± 0.2 | 1.9 ± 0.2 | 3.5 ± 0.2 |
| "NOVANTRONE" | | | | | | | |
| 0.5 | 9 | 0 ± 0* | 0 ± 0* | 0 ± 0* | 0 ± 0* | 0 ± 0* | 0.2 ± 0.2* |
| 0.25 | 9 | 0.3 ± 0.2* | 0.3 ± 0.2* | 0.3 ± 0.2* | 0 ± 0* | 0 ± 0* | 1.2 ± 0.4* |
| Cyclophosphamide | | | | | | | |
| 5 | 9 | 0 ± 0* | 0 ± 0* | 0 ± 0* | 0 ± 0* | 0.25 ± 0.2* | 1.0 ± 0.4* |
| 2.5 | 9 | 0.6 ± 0.0* | 0.6 ± 0.0* | 0 ± 0* | 0.6 ± 0.4* | 0.6 ± 0.4* | 2.9 ± 0.3 |
| 1.25 | 9 | 0.3 ± 0.2* | 1.0 ± 0.3* | 2.1 ± 0.4 | 2.3 ± 0.4 | 2.6 ± 0.2 | 2.4 ± 0.2 |

*$p \leq 0.05$ as compared to controls.
**Treatment with "NOVANTRONE" or cyclophosphamide was initiated on day 7 post immunization.

Since rats sensitized with myelin basic protein (MBP) and treated with "NOVANTRONE" at 0.5 mg/kg/day did not develop clinical or histological signs of EAE, as shown by the results in Table I, a test was performed on these animals to determine if their spleens contained MBP-sensitized T cells (pre-T effector cells) that developed or proliferated into T effector cells upon culture with MBP as described by Killen, J. A. and Swanborg, R. H., J. Immunol., 129, 759(1982). The results of this test show (in Table IV) that sensitized spleen cells from "NOVANTRONE"—treated animals did not transfer EAE (clinical symptoms or histological lesions) to naive syngeneic recipients. The data also indicate that following "NOVANTRONE" treatment, spleens of the treated animals were devoid of MBP-sensitive T cells. Furthermore, adoptive transfer of the disease did not occur even when the spleen cells of "NOVANpassive transfer of EAE (Panitch, H. S., Cell. Immunol., 56, 163(1980)), it is believed that "NOVANTRONE" in vitro prevents the conversion of MBP-sensitized T cells to T effector cells.

TABLE V

In Vitro Incubation of MBP-Sensitized Cells with "NOVANTRONE" Abolishes Their Capacity to Transfer EAE to Naive Recipients

| In Vitro Treatment of cells | No. of Recipients | Paralysis Grade (±SEM) | Incidence of Paralysis | Histological Grade* (±SEM) |
|---|---|---|---|---|
| MBP | 6 | 1.2 ± 0.2 | 6/6 | 1.6 ± 0.3 |
| MBP + "NOVANTRONE" (0.1 μg/ml) | 5 | 0 ± 0* | 0/5* | 0 ± 0* |

TABLE V-continued

In Vitro Incubation of MBP-Sensitized Cells with "NOVANTRONE" Abolishes Their Capacity to Transfer EAE to Naive Recipients

| In Vitro Treatment of cells | No. of Recipients | Paralysis Grade (±SEM) | Incidence of Paralysis | Histological Grade* (±SEM) |
| --- | --- | --- | --- | --- |
| MBP + "NOVANTRONE" (0.01 μg/ml) | 5 | 0 ± 0* | 0/5* | 0 ± 0* |

*p ≦ 0.05 as compared to MBP controls.

Normal rats were pretreated with saline or "NOVANTRONE" for 5 days. Treatment was stopped and the rats were injected intraperitoneally with spleen cells from EAE animals, the cells having been incubated in vitro for 72 hours with MBP. Paralysis Grade, Incidence of Paralysis and Spinal Cord Histopathology were determined on day 7 post transfer.

Spleen cells from challenged animals failed to transfer EAE (clinical symptoms and histological lesions) to recipients pretreated for 5 days with 0.5 mg/kg/day "NOVANTRONE" as shown in Table VI. If effector cell proliferation in the host is essential, as has been suggested, then recipients pretreated with "NOVANTRONE" cannot support this proliferation.

TABLE VI

Rats Pretreated with "NOVANTRONE" Do Not Develop EAE Lesions Upon the Administration of MBP-Sensitized Spleen Cells

| Pretreatment of Recipients | No. of Rats | Paralysis Grade (±SEM) | Incidence of Paralysis | Histological Grade (±SEM) |
| --- | --- | --- | --- | --- |
| Saline | 3 | 1.0 ± 0 | 3/3 | 3.3 ± 0.3 |
| "NOVANTRONE" (0.5 mg/kg) | 3 | 0 ± 0 | 0/3* | 0 ± 0* |

*p ≦ 0.05 as compared to saline-pretreated controls.

The effect of "NOVANTRONE" on rapid passive EAE was also investigated. Rats with pre-existing thermal brain injuries developed histological lesions of EAE by 24 hours after treatment with sensitized lymph node cells. EAE lesions were absent in those animals that received a single dose of "NOVANTRONE" at 1.0 or 0.5 mg/kg before cell transfer.

The above studies show that "NOVANTRONE", when administered intraperitoneally, suppresses the clinical symptoms and histological lesions associated with the active and passive forms of EAE. These comparative studies have shown that "NOVANTRONE" is 10 to 20 times more potent than cyclophosphamide in the suppression of EAE.

"NOVANTRONE" suppresses the clinical symptoms and histological lesions of EAE when administered intraperitonealy in amounts ranging from about 0.25 mg/kg to about 0.5 mg/kg of body weight per day. A preferred dosage regimen for optimum results would be from about 0.25 to about 0.5 mg/kg of body weight per day and dosage units should be employed such that a total of from about 17.5 mg to about 35 mg of "NOVANTRONE" are administered to a subject of about 70 kg of body weight in a 24-hour period. This dosage regimen may be adjusted to provide the optimum therapeutic response. For example, several divided doses may be administered daily or the dose may be proportionally reduced as indicated by the exigencies of the therapeutic situation.

"NOVANTRONE" may be administered parenterally, in particular, intraperitoneally. Solutions of "NOVANTRONE" can be prepared in water suitably mixed with a surfactant such as hydroxypropylcellulose. Dispersions can also be prepared in glycerol, liquid polyethylene glyocos and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions under the conditions of manufacture and storage and must be preserved against the contaminating action of microorganisms such as bacteria and fungi. The carrier can be a solvent or dispersion medium containing for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various anti-bacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum drying and the freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional medium or agent is incompatible with the active ingredient, its use in the therapeutic compositions is contemplated.

It is especially advantageous to formulate parenteral compositions in dosage unit form for ease of administration and uniformity of dosage. Dosage unit form, as used herein, refers to physically discrete units suited as unitary dosages for the mammalian subjects to be treated, each unit containing a predetermined quantity of active material calculated to produce the desired therapeutic effect in association with the required pharmaceutical carrier. The specification for the novel dosage unit forms of the invention are dictated by, and directly dependent on, the unique characteristics of the active material and the particular therapeutic effect to be achieved, and the limitations inherent in the art of compounding such an active material for the treatment of disease in living subjects having a diseased condition in which bodily health is impaired as herein disclosed in detail.

What is claimed is:

1. A method of treating neuroimmunologic diseases in a mammal which comprises administering parenterally to said mammal from about 0.25 to about 0.5 mg per kilogram of body weight per day of a compound selected from 1,4-dihydroxy-5,8-bis[[2-(2-hydroxethylamino)ethyl]amino]-anthraquinone and the pharmacologically acceptable acid addition salts thereof.

2. A method according to claim 1, wherein the compound is 4-dihydroxy-5,8-bis[[2-(2-hydroxyethylamino)ethyl]amino]anthraquinone, dihydrochloride.

3. A method according to claim 1, wherein the compound is administered intraperitoneally.

4. A method according to claim 1, wherein the neuroimmunologic disease is multiple sclerosis.

5. A method according to claim 1, wherein the neuroimmunologic disease is acute disseminated encephalomyelitis.

6. A method of treating neuroimmunologic diseases in mammals which comprises administering parenterally an sufficient amount of 1,4-dihydroxy-5,8-bis[[2-(2-hydroxyethylamino)ethyl]amino]anthraquinone or a pharmacologically acceptable acid addition salt thereof to palliate muscular weakness and paralysis symptomatic of these diseases in said mammals.

7. A method according to claim 6, wherein the neuroimmunologic disease is multiple sclerosis.

8. A method according to claim 6, wherein the neuroimmunologic disease is acute disseminated encephalomyelitis.

* * * * *